United States Patent [19]

Rothlein et al.

[11] Patent Number: 5,162,371

[45] Date of Patent: Nov. 10, 1992

[54] METHOD FOR TREATING INFLAMMATION

[75] Inventors: Robert Rothlein, Danbury, Conn.; Ronald Faanes, Pound Ridge, N.Y.; Genus Possanza, Ridgefield, Conn.

[73] Assignee: Boehringer Ingelheim Pharmaceuticals, Inc., Ridgefield, Conn.

[21] Appl. No.: 683,917

[22] Filed: Apr. 11, 1991

Related U.S. Application Data

[62] Division of Ser. No. 477,785, Feb. 9, 1990, Pat. No. 5,028,630.

[51] Int. Cl.$^5$ .................. A61K 21/24; A61K 31/195; A61K 31/275

[52] U.S. Cl. ..................... 514/524; 514/561; 514/535

[58] Field of Search .......... 514/535, 561, 524

*Primary Examiner*—S. J. Friedman

*Attorney, Agent, or Firm*—David E. Frankhouser; Daniel Reitenbach; Alan R. Stempel

[57] ABSTRACT

A method for treating inflammation in a patient which comprises administering to the patient a therapeutically effective amount of a compound of the formula:

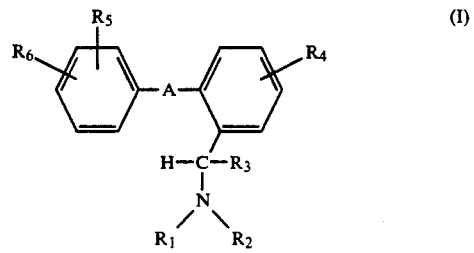

wherein A and $R_1$–$R_6$ are defined herein.

2 Claims, No Drawings

METHOD FOR TREATING INFLAMMATION

This is a division of application Ser. No. 477,785, filed Feb. 9, 1990, U.S. Pat. No. 5,028,630.

FIELD OF THE INVENTION

This invention is related to a method for treating inflammation using certain benzylamine compounds.

BACKGROUND

Benzylamines are known in the art. U.S. Pat. No. 3,635,974 describes α-phenyl-2-aminomethyl-benzylalcohols useful as anorectics in warm-blooded animals. U.S. Pat. No. 3,728,460 describes anorectic pharmaceutical compositions containing certain 2-(methylaminomethyl)-α-(4'-halophenyl)-benzyl alcohols as active ingredients. In Freter et al, "A New Group of Anorexingenic Compounds", J. Med. Chem 13, 1228 (1970), there is described the structure and anoxerigenic activity of a group of substituted aminomethylbenzhydrols. Benzylamine compounds are also described in British Patent No. 984,363; French Patent No, 1,549,342; Netherlands Patent No. 6,606,390; German Offenlegungeschrift 2834312; Freter et al, "2-Aminomethylbenzhydrols", Can. J. Chem. 48 (11), 1670 (1970); and Freter et al, "A New Tetrahydroisoquinoline Synthesis", J. Het. Chem 7, 159 (1970).

It is the purpose of this invention to describe the use of certain benzylamine compounds in the treatment of inflammation.

DESCRIPTION OF THE INVENTION

This invention relates to a method for treating inflammation in a patient requiring such treatment, which comprises administering to the patient a therapeutically effective amount of a compound of the formula:

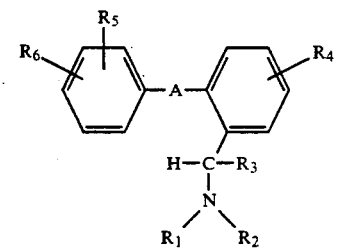

wherein
- $R_1$ and $R_2$ are each hydrogen, alkyl of from 1 to 4 carbon atoms, or hydroxyalkyl of from 1 to 4 carbon atoms;
- $R_3$ is hydrogen or alkyl of form 1 to 4 carbon atoms;
- $R_4$ is hydrogen, halogen, alkyl of from 1 to 4 carbon atoms, hydroxy, or alkoxy of from 1 to 4 carbon atoms;
- $R_5$ is hydrogen, halogen, hydroxy, amino, nitro, nitrile, amino-methyl, carboxyl, trifluoromethyl, alkyl of from 1 to 4 carbon atoms, alkoxy of from 1 to 4 carbon atoms, alkylamino of from 1 to 6 carbon atoms, alkylthio of from 1 to 4 carbon atoms, alkylaminomethyl of from 2 to 5 carbon atoms, or —$COOR_8$;
- $R_6$ is alkyl of from 1 to 7 carbon atoms, hydroxyl, hydrogen, or $OR_7$;
- $R_7$ is alkyl of from 1 to 7 carbon atoms;
- $R_8$ is alkyl of from 1 to 4 carbon atoms; and

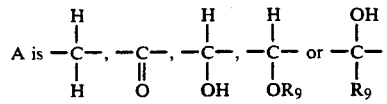

wherein $R_9$ is alkyl of from 1 to 4 carbon atoms.

For the purpose of this invention, "inflammation" shall mean any physiological process which involves the recruitment and/or activation of leucocytes. Examples of inflammation treatable in accordance with the present invention include inflammation associated with skin infections, autoimmune states, and granulomatos diseases, such as tuberculosis, sarcoidosis and Crohne's Disease.

Preferably, in the method of this invention,
- $R_1$ is hydrogen, methyl or ethyl;
- $R_2$ is hydrogen, methyl or ethyl;
- $R_3$ is hydrogen or methyl;
- $R_4$ is hydrogen, halogen or methyl;
- $R_5$ is hydrogen, halogen, methyl, $OSCH_3$, or trifluoromethyl; $R_6$ is hydrogen, halogen, methyl or trifluoromethyl; and

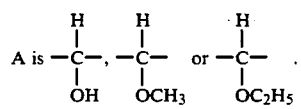

Most preferably,
- R1 is methyl;
- R2 is hydrogen or methyl:
- R3 is hydrogen;
- R4 is hydrogen;
- R5 is fluorine or chlorine;
- R6 is hydrogen; and

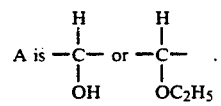

The compounds useful in the method of this invention can be prepared by various methods involving known chemical synthesis principals [see e.g., Freter et al, Can. J. Chem. 48 (11), 1670 (1970)]. Preferred methods include the following:

METHOD A

A phenylpthalide of the formula

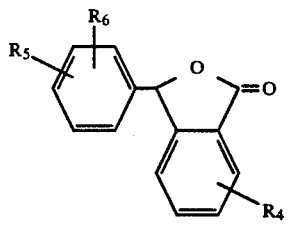

is reacted with an amine of the formula

in a solvent such alcohol, benzene, toluene or xylene, to produce an amide of the formula:

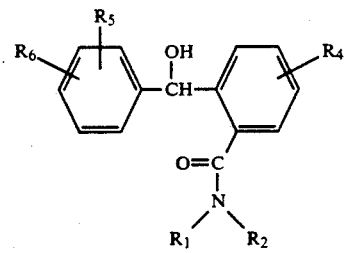

The amide is reduced with lithium aluminum hydride, or with some other complex metal hydride, to produce a compound of Formula I.

METHOD B

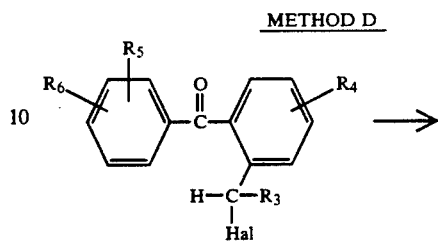

An isoindoline (II) is dissolved in an acyl anhydride or dissolved with an acyl anhydride in a suitable solvent and then preferably refluxed, to produce a diacylated compound (III). The diacylated compound (III) is heated in the presence of a base such as an alkali metal hydroxide, to produce a compound of Formula I.

METHOD C

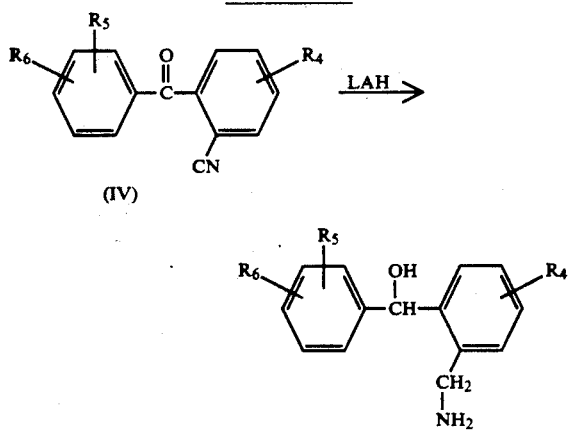

Compound IV is reduced in the presence of a suitable reducing agent such as lithium aluminum hydride or other complex metal hydride, to produce a compound of Formula I. The resulting compound of Formula I can then be alkylated, acylated, etherified or esterified [see Freter et al, Can J. Chem. 48 (11), 1670 (1970)].

METHOD D

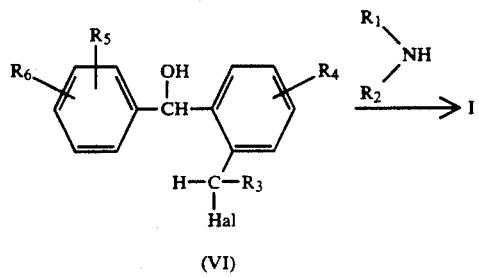

Compound (V) in a suitable solvent such as alcohol, is reduced in the presence of a suitable reducing agent such as sodium borohydride, to produce Compound VI. Compound VI is then reacted with a suitable amine to produce a compound of Formula I.

The compounds useful in the method of this invention can exist steriometrically as S isomers, R isomers or as diasteriometric mixtures of R and S isomers, with A as the chiral center. Preferred compounds are those which are the negative rotating isomers.

The compounds of this invention can be administered to treat inflammation by any means or route of administration that produces contact of the compound with its site of action in the body of the individual human or animal under treatment. The compound can be administered by know conventional routes of administration such as by oral administration, or injection. The compound is usually administered in dosage forms which deliver it in a conventional pharmaceutical carrier or mixtures thereof which are selected on the basis of the particular route of administration and rate of delivery to the site of action which is desired.

Dosage forms (compositions) which are suitable for internal administration of the compounds include oral administration forms such as tablets, coated tablets, capsules, syrups, elixirs or suspensions. Such carriers for each route of administration are described in Remington's Pharmaceutical Sciences.

The range of dosages in which the compound in accordance with the invention can be administered will vary depending upon the route of administration selected as well as the characteristics of the intended recipient, including age,m body weight, general state of health and the like. Usually, the compound of the invention is administered in unit doses of from about 1 to about 100 mgs and from about 1 to about 4 times daily. Such unit doses can be combined in metered release dosage forms for sustained single dose release of the compound.

EXAMPLE 1

Reverse Passive Arthus Reaction

The reverse passive Arthus reaction is initiated by the interaction of antigen and antibody resulting in the formation of a precipitating immune complex, followed by fixation of complement, accumulation of leukocytes, edema and hemorrhage. The immunopathology of rheumatoid arthritis involves many of the parameters found in this reaction.

Test groups (5 rats per group) are dosed orally with compounds one hour prior to the sub-plantar injection into the right hind paw of rabbit anti-ovalbumin antibody (50 µg/0.1 ml). Immediately afterwards, ovalbumin (Sigma, #5503) (5 mg/0.2 ml) is injected i.v. via the tail vein. The right hind paw volume is measured at hourly intervals, from one to four hours after the injection of the immune reactants.

The change in paw volume for each animal is calculated by subtracting zero hour paw volume (before injection) from the paw volume at the time of measurement. The mean of these values is calculated for each group. Results are expressed in Table I below as percent inhibition of paw swelling compared to untreated controls.

For the purposes of Table I, the following compounds will have the following numerical designations:

| COMPOUND DESIGNATION | COMPOUND NAME |
|---|---|
| 1 | 2-(N-methylamino)methyl-α-(4-methoxyphenyl) benzyl alcohol |
| 2 | 2-(N-methylamino)methyl-α-(4-chlorophenyl)benzyl alcohol |
| 3 | 2-(N,N-dimethylamino)methyl-α-(4-chlorophenyl) benzyl alcohol |
| 4 | α-[2-(N-methylamino methyl)phenyl-4-chloro benzyl ethyl ether |
| 5 | 2-(N-Butylamino)methyl-α-(4-chlorophenyl)benzyl alcohol |
| 6 | 2-(N-methylamino)methyl-α-(4-methylphenyl)benzyl alcohol |
| 7 | 2-(N-methylamino)methyl-α-(4-fluorophenyl)benzyl alcohol |
| 8 | 2-(N-methylamino)methyl-α-(2-chlorophenyl)benzyl alcohol |
| 9 | 2-(N-hydroxyethylamino)methyl-α-(4-chlorophenyl)benzyl alcohol |
| 10 | 2-(N-methylamino)methyl-α-(4-chloro-3-trifluoromethyl)benzyl alcohol |
| 11 | 2-(N-ethylamino)methyl-α-(4-chlorophenyl) benzyl alcohol |
| 12 | 2-(aminomethyl)-α-phenylbenzyl alcohol |
| 13 | 2-(N-methylamino)methyl-α-phenylbenzyl alcohol |
| 14 | 4-chloro-2'-methylaminomethyldiphenylmethane hydrochloride |
| 15 | *2-(N-methylamino)methyl-α-(4-chlorophenyl) benzyl alcohol ([α] +78°) |
| 16 | *2-(N-methylamino)methyl-α-(4-chlorophenyl) benzyl alcohol ([α] −80°) |
| 17 | *2-(N-methylamino)methyl-α-(4-fluorophenyl)benzyl alcohol ([α] +73.3°) |
| 18 | *2-(N-methylamino)methyl-α-(4-fluorophenyl)benzyl alcohol ([α] −74.4°) |
| 19 | *2-(N,N-dimethylamino)methyl-α-(4-chlorophenyl)benzyl alcohol ([α] +46°) |
| 20 | *2-(N,N-dimethylamino)methyl-α-(4-chlorophenyl)benzyl alcohol ([α] −46°) |
| 21 | *2-(N,N-dimethylamino)methyl-α-(4-fluorophenyl)benzyl alcohol ([α] +55°) |
| 22 | *2-(N,N-dimethylamino)methyl-α-(4-fluorophenyl)benzyl alcohol ([α] −53°) |
| 23 | 2-aminomethyl-5-chlorobenzhydrol hydrochloride |
| 24 | 4-chloro-2'-(1-methylaminomethyl)benzhydrol hydrochloride |
| 25 | 2-(N-methylamino)methyl-α-(4-cyanophenyl) benzyl alcohol |
| 26 | 2-(N-methylamino)methyl-α-(4-aminomethylphenyl) benzyl alcohol |
| 27 | 2-(N,N-dimethylamino)methyl-α-(4-fluorophenyl)benzyl alcohol |
| 28 | 2-(aminomethyl)methyl-α-(4-fluorophenyl) benzyl alcohol |
| 29 | 2-(N,N-dipropylamino)methyl-α-(4-fluorophenyl) benzyl alcohol |
| 30 | 4'-Fluoro-2-(methylaminomethyl) diphenylmethane hydrochloride |
| 31 | 2-(N-methylamino)methyl-α-(2,6-difluorophenyl) benzyl alcohol |
| 32 | 2-(N,N-dimethylamino)methyl-α-(4-fluoro-2-methylphenyl) benzyl alcohol |
| 33 | 2-(N-methylamino)methyl-α-(4-fluoro-2-methylphenyl) benzyl alcohol |
| 34 | 2-(N,N-dimethylamino)methyl-α-(4-nitrophenyl) benzyl alcohol |
| 35 | 2-(N,N-dimethylamino)methyl-α-(4-trifluoromethylphenyl) benzyl alcohol |
| 36 | α-[2,(N,N-dimethylaminomethyl)phenyl]-4-hydroxybenzyl ethyl ether |
| 37 | 2-(N,N-dimethylamino)methyl-α-(3,4-dichlorophenyl)benzyl alcohol |

*Rotational isomer

TABLE I

| COMPOUND (DOSAGE 30 mg/kg) | % INHIBITION (HOUR) | | |
|---|---|---|---|
| | 2 | 3 | 4 |
| 1 | 28 | 20 | 5 |
| 2 | 71 | 75 | 79 |
| 3 | 81 | 79 | 67 |
| 4 | 72 | 73 | 65 |
| 5 | 28 | 30 | 29 |
| 6 | 63 | 47 | 27 |
| 7 | 66 | 72 | 75 |
| 8 | 53 | 55 | 48 |
| 9 | 23 | 16 | 10 |
| 10 | 66 | 40 | 16 |
| 11 | 65 | 57 | 54 |
| 12 | 49 | 12 | 0 |
| 13 | 69 | 40 | 17 |
| 14 | 66 | 62 | 40 |
| 15 | 69 | 61 | 56 |
| 16 | 67 | 61 | 30 |
| 17 | 81 | 78 | 79 |
| 18 | 70 | 49 | 26 |
| 19 | 77 | 71 | 68 |
| 20 | 57 | 45 | 20 |
| 21 | 61 | 64 | 61 |
| 22 | 56 | 29 | 12 |
| 23 | 46 | 27 | 19 |
| 24 | 51 | 47 | 26 |
| 25 | 58 | 62 | 39 |
| 26 | 39 | 34 | 18 |
| 27 | 91 | 77 | 58 |
| 28 | 81 | 82 | 72 |
| 29 | 63 | 33 | 18 |
| 30 | 53 | 48 | 30 |
| 31 | 46 | 26 | 18 |
| 32 | 50 | 28 | 20 |
| 33 | 56 | 52 | 24 |
| 34 | 38 | 25 | 19 |
| 35 | 43 | 39 | 8 |
| 36 | 52 | 36 | 27 |
| 37 | 58 | 52 | 61 |

What is claimed is:

1. A method for treating inflammation in a patient requiring such treatment, which comprises administering to the patient a therapeutically effective amount of a compound of the formula

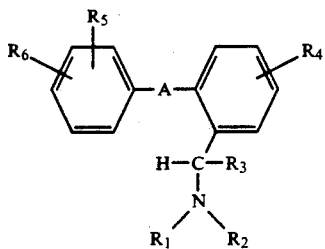 (I)

wherein $R_1$ and $R_2$ are each hydrogen, alkyl of from 1 to 4 carbon atoms, or hydroxyalkyl of 1 to 4 carbon atoms;

$R_3$ is hydrogen or alkyl of from 1 to 4 carbon atoms;

$R_4$ is hydrogen, halogen, alkyl of from 1 to 4 carbon atoms, hydroxy, or alkoxy of from 1 to 4 carbon atoms;

$R_5$ is nitrile, carboxyl, or —$COOR_8$;

$R_6$ is alkyl of from 1 to 7 carbon atoms, hydroxyl, hydrogen, or $OR_7$;

$R_7$ is alkyl of from 1 to 7 carbon atoms;

$R_8$ is alkyl of from 1 to 4 carbon atoms; and

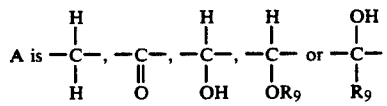

wherein $R_9$ is alkyl of from 1 to 4 carbon atoms, or a physiologically acceptable salt of the compound.

2. A method as recited in claim 1 wherein the patient is human.